(12) United States Patent
Li et al.

(10) Patent No.: US 11,969,370 B2
(45) Date of Patent: Apr. 30, 2024

(54) MEDICAL DEVICE IMPLANTATION APPARATUS

(71) Applicant: Micro-Tech (Nanjing) Co., Ltd., Jiangsu (CN)

(72) Inventors: Yuqian Li, Jiangsu (CN); Huan Liu, Jiangsu (CN); Derong Leng, Jiangsu (CN); Yongxue Zhao, Jiangsu (CN); Changqing Li, Jiangsu (CN); Chunjun Liu, Jiangsu (CN)

(73) Assignee: Micro-Tech (Nanjing) Co., Ltd., Jiangsu (CN)

( * ) Notice: Subject to any disclaimer, the term of this patent is extended or adjusted under 35 U.S.C. 154(b) by 576 days.

(21) Appl. No.: 17/272,448

(22) PCT Filed: Aug. 23, 2019

(86) PCT No.: PCT/CN2019/102165
§ 371 (c)(1),
(2) Date: Mar. 1, 2021

(87) PCT Pub. No.: WO2020/048325
PCT Pub. Date: Mar. 12, 2020

(65) Prior Publication Data
US 2021/0322192 A1 Oct. 21, 2021

(30) Foreign Application Priority Data
Sep. 3, 2018 (CN) .......................... 201811017972.6

(51) Int. Cl.
*A61F 2/966* (2013.01)

(52) U.S. Cl.
CPC .................................. *A61F 2/966* (2013.01)

(58) Field of Classification Search
CPC .. A61F 2/856; A61F 2/95; A61F 2/954; A61F 2/958; A61F 2/962; A61F 2/966;
(Continued)

(56) References Cited

U.S. PATENT DOCUMENTS 6,514,281 B1 * 2/2003 Blaeser .................... A61F 2/954
623/1.35
8,337,542 B2 12/2012 Jantzen et al.
(Continued)

FOREIGN PATENT DOCUMENTS

CN 203677329 U 7/2014
CN 105943092 A 9/2016
(Continued)

*Primary Examiner* — Robert A Lynch
(74) *Attorney, Agent, or Firm* — Peter W. Schroen; Bret E. Field; Bozicevic, Field & Francis LLP

(57) ABSTRACT

Provided is a medical device implantation apparatus, comprising: an outer sheath, connected to a first portion of a handle and extending from a proximal end to a distal end; a middle sheath, the middle sheath being arranged in the outer sheath, and the middle sheath being connected to a second portion of the handle; an inner sheath, the inner sheath being allowed to pass through the middle sheath, the inner sheath being connected to a third portion of the handle, and the inner sheath being movable relative to the outer sheath; outer casings, with at least two outer casings being provided, and a distal end of the inner sheath being respectively fixedly connected to the outer casings; and a medical device, arranged around the inner sheath and partially accommodated in the outer casings.

9 Claims, 5 Drawing Sheets

(58) Field of Classification Search
CPC .......... A61F 2/9661; A61F 2/9662; A61F 2002/065; A61F 2002/9505; A61F 2002/9623; A61F 2002/9665; A61M 25/104; A61M 2025/1045
See application file for complete search history.

(56) References Cited

U.S. PATENT DOCUMENTS

| | | | |
|---|---|---|---|
| 2006/0293695 A1* | 12/2006 | Ricci | A61F 2/954 623/1.11 |
| 2010/0274339 A1 | 10/2010 | Muzslay | |
| 2012/0016454 A1 | 1/2012 | Jantzen et al. | |
| 2016/0256303 A1 | 9/2016 | Bourang | |
| 2016/0374842 A1* | 12/2016 | Havel | A61F 2/9662 606/108 |

FOREIGN PATENT DOCUMENTS

| | | |
|---|---|---|
| CN | 106420129 A | 2/2017 |
| EP | 1187577 A1 | 3/2002 |
| EP | 2036519 A1 | 3/2009 |
| EP | 2777653 A1 | 9/2014 |

\* cited by examiner

MEDICAL DEVICE IMPLANTATION APPARATUS

FIELD OF THE PRESENT DISCLOSURE

The invention relates to a medical device, in particular to a medical device implantation apparatus.

BACKGROUND OF THE PRESENT DISCLOSURE

For patients with cavity stenosis caused by advanced lung cancer, patients with lumen external pressure type stenosis caused by mediastinal and esophageal tumors, and patients with tumors who are old and cannot tolerate surgery in poor general conditions, the emergence of Y-shaped stents solves the complications of lumen stenosis and stent displacement very well.

For implanting a traditional Y-shaped stent implantation apparatus, firstly, a front handle is withdrawn to extend branches of a Y-shaped stent, then, the branches of the stent are released by loosening binding wires, a positioning lock is unscrewed, and the front handle is continuously withdrawn to completely release the stent. The operation process is cumbersome, and the operation takes a long time. The knots of the binding wires cause certain damage to erosive tissues. The release of a pulling wire requires a certain force, which tends to shift the stent shift, and results in the failure of operation. The binding wires need sufficient tensile strength, otherwise the binding wires may break during the operation to cause the failure of the device. When the stent is bound, the binding wires need to be knotted with slipknots one by one, otherwise the binding wires cannot be loosened during the operation to cause the failure of operation.

Therefore, there is an urgent need for an implantation apparatus that is easy to operate and can effectively release the stent, so as to solve the problems that the traditional stent implantation apparatus is difficult to operate and the operation takes too much time, and to overcome a series of safety hazards caused by the binding wires.

SUMMARY OF THE PRESENT DISCLOSURE

The purpose of the present invention is to design a medical device implantation apparatus, which is suitable for a medical device with branches, such as Y-shaped stents. By constraining the distal end of the medical device product, the effect of positioning the distal end of the medical device is achieved. The operation is easier, so that the operation time is shortened while the damage to the tumor tissue is reduced, and the patient's pain is reduced. Moreover, the probability of apparatus failure is reduced.

The invention provides a medical device implantation apparatus. The medical device implantation apparatus comprises an outer sheath, a middle sheath, an inner sheath, outer casings, and a medical device, wherein the outer sheath is connected to a first portion of a handle and extends from a proximal end to a distal end; the middle sheath is arranged in the outer sheath, and is connected to a second portion of the handle; the inner sheath is allowed to pass through the middle sheath and is connected to a third portion of the handle, and the inner sheath is movable relative to the outer sheath; the number of the outer casings is at least two; a distal end of the inner sheath is respectively fixedly connected to the outer casings; and the medical device is arranged around the inner sheath and partially accommodated in the outer casings. The inner sheath moves relative to the outer sheath by manipulating the third portion of the handle to release the medical device.

According to the medical device implantation apparatus of the invention, the outer casing includes a part for fixing the inner sheath and a part for fixing the medical device.

According to the medical device implantation apparatus of the invention, the inner sheath includes a first inner sheath and a second inner sheath which are distributed side by side, and the tail end of the distal end of the inner sheath is respectively connected to the outer casings.

According to the medical device implantation apparatus of the invention, the first inner sheath and the second inner sheath are the same in length or different in length.

According to the medical device implantation apparatus of the invention, the inner sheath has a distal end bifurcation structure that is respectively connected to the outer casings.

According to the medical device implantation apparatus of the invention, the medical device is a stent.

According to the medical device implantation apparatus of the invention, the middle sheath is connected to the second portion of the handle through a booster sheath.

According to the medical device implantation apparatus of the invention, the booster sheath is made of metal.

According to the medical device implantation apparatus of the invention, a positioning lock is arranged between the first portion of the handle and the second portion of the handle.

According to a method of using the medical device implantation apparatus of the invention, the first portion of the handle is withdrawn towards the proximal end, and part of the medical device is released from the outer sheath; then the third portion of the handle is pushed towards the distal end, and the medical device is separated from the outer casings; and finally, the first portion of the handle is withdrawn, and the medical device is released and implanted.

Figure 1:
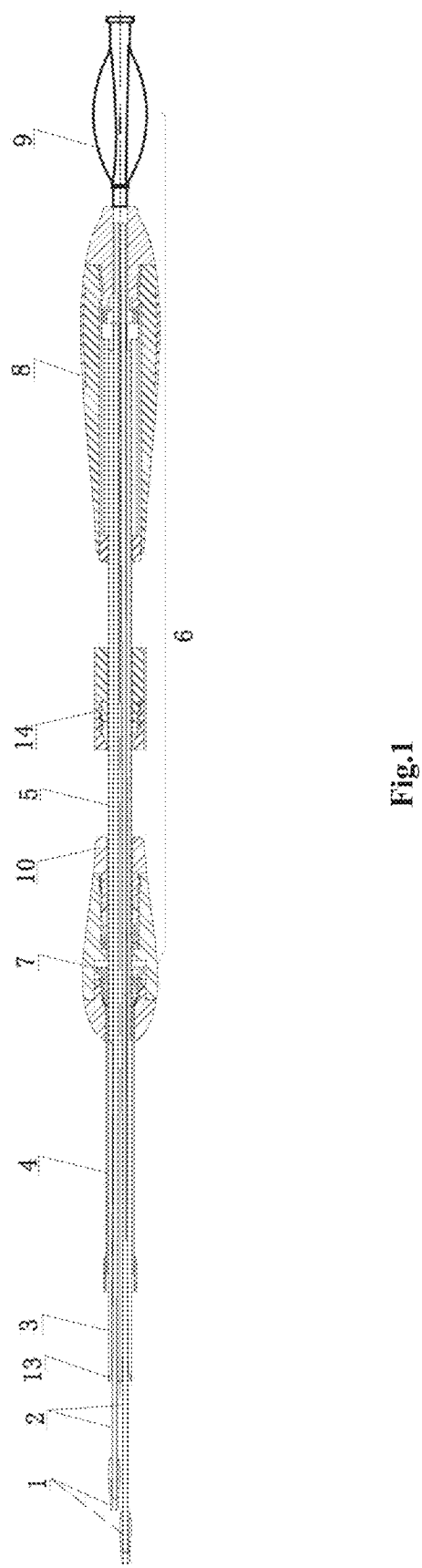
FIG. 1 is a schematic diagram of a medical device implantation apparatus of the present invention.
Figure 2:
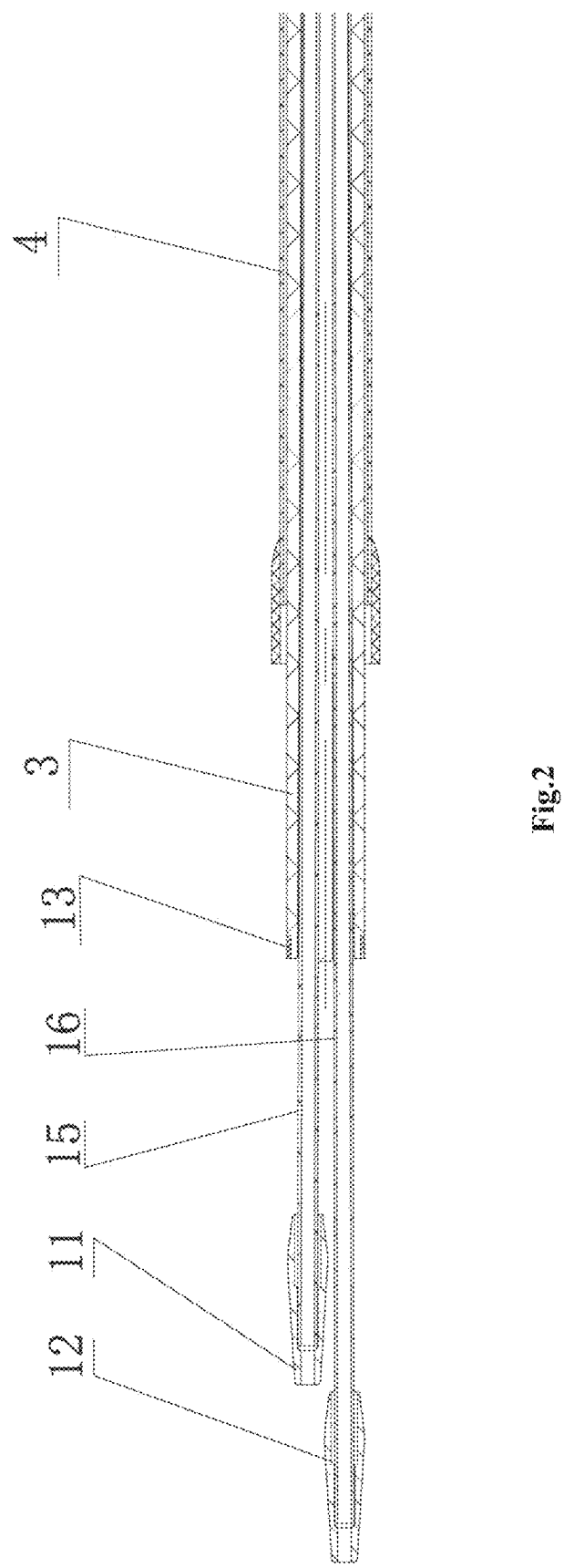
FIG. 2 is an enlarged view of the distal end of the medical device implantation apparatus of the present invention.

LIST OF REFERENCE NUMERALS IN THE DRAWINGS 1 outer casing
2 inner sheath
3 middle sheath
4 outer sheath
5 booster sheath
6 handle
7 front handle part
8 rear handle part
9 adjusting handle
10 safety lock
11 first outer casing
12 second outer casing
13 developing part 14 positioning lock
15 first inner sheath
16 second inner sheath
21 distal end inner hole
22 middle section inner hole
23 proximal end inner hole
30 stent main branch
31, 32 stent branches

DESCRIPTION OF THE EMBODIMENTS

The technical solution of the present invention is described in detail below with reference to the accompanying drawings. It should be understood that the specific embodiments described herein are only used to explain the present invention, and not to limit the present invention. The scope of the application is not limited by these embodiments, but the scope of the patent application shall prevail. In order to provide a clearer description and enable those familiar with the art to understand the application content of the present application, the various parts in the figures are not necessarily drawn according to their relative dimensions, and the ratio of certain dimensions to other relevant dimensions is highlighted and exaggerated. The details that are irrelevant or unimportant are not completely drawn in order to keep the diagram concise.

The invention provides a medical device implantation apparatus. The medical device implantation apparatus comprises an outer sheath, a middle sheath, an inner sheath, outer casings, and a medical device, wherein the outer sheath is connected to a first portion, namely, a front handle part, of a handle and extends from a proximal end to a distal end; the middle sheath is arranged in the outer sheath, and is connected to a second portion, namely, a rear handle part, of the handle; the inner sheath is allowed to pass through the middle sheath and is connected to a third portion, namely, an adjusting handle, of the handle, and is movable relative to the outer sheath; the number of the outer casings is at least two; a distal end of the inner sheath is respectively fixedly connected to the outer casings; and the medical device is arranged around the inner sheath and partially accommodated in the outer casings. The inner sheath moves relative to the outer sheath by manipulating the third portion of the handle to release the medical device.

According to the medical device implantation apparatus of the invention, the outer casing includes a part for fixing the inner sheath and a part for fixing the medical device. The part for fixing the inner sheath and the part for fixing the medical device can be of the same structure or different structures.

According to the medical device implantation apparatus of the invention, the inner sheath includes a first inner sheath and a second inner sheath which are distributed side by side, and the tail end of the distal end of the inner sheath is respectively connected to the outer casings. Preferably, the inner sheath is fixed in a middle section inner hole of the outer casing; and the medical device is partially arranged between the inner sheath and the outer casings.

According to the medical device implantation apparatus of the invention, the first inner sheath and the second inner sheath are the same in length or different in length.

According to the medical device implantation apparatus of the invention, the inner sheath can have a cavity at the proximal end and a bifurcation structure at the distal end, and the tail end of the bifurcation structure of the inner sheath is respectively connected to the outer casings.

According to the medical device implantation apparatus of the invention, the medical device is a stent, and the medical device can also be a medical catheter.

According to the medical device implantation apparatus of the invention, the middle sheath is connected to the second portion of the handle through a booster sheath, and the proximal end of the middle sheath is fixedly connected to the booster sheath and then connected to the handle. The proximal end of the middle sheath can also be directly connected to the handle.

According to the medical device implantation apparatus of the invention, the booster sheath is made of metal, including medical stainless steel.

According to the medical device implantation apparatus of the invention, a positioning lock is arranged between the first portion of the handle and the second portion of the handle.

According to a using method of the medical device implantation apparatus of the invention, the first portion of the handle is withdrawn towards the proximal end, and part of the medical device is released from the outer sheath, specifically, branch parts of the medical device assembled in the outer sheath are separated from the outer sheath; then the third portion of the handle is pushed towards the distal end, and the medical device is separated from the outer casings, specifically, the medical device assembled in the outer casings is separated from the outer casings; and finally, the first portion of the handle is withdrawn, the main branch of the medical device is withdrawn from the outer sheath, and the release and implantation are completed.

As shown in FIG. 1 to FIG. 4, the present invention provides a medical device implantation apparatus, which includes an outer casings 1, an inner sheath 2, a middle sheath 3, an outer sheath 4, a booster sheath 5, and a handle 6, wherein the handle 6 includes three parts, specifically the front handle part 7, the rear handle part 8, and the adjusting handle 9.

Figure 3:
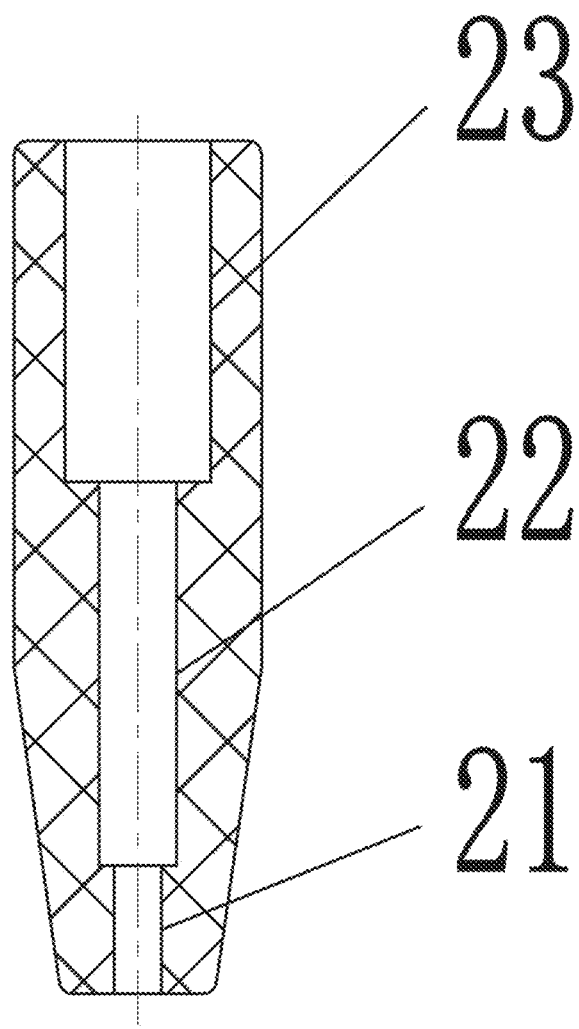
FIG. 3 is a cross-sectional view of an outer casing of the medical device implantation apparatus shown in FIG. 1.

The number of the outer casings 1 can be two or more. The outer casings 1 comprises at least a first outer casing 11 and a second outer casing 12. The first outer casing 11 and the second outer casing 12 can be of one-stage type structures, two-stage type structures or three-stage type structures, and are used for fixing the inner sheath 2 and containing the medical device. Preferably, as shown in FIG. 3, the first outer casing 11 and the second outer casing 12 are of hollow three-stage structures, and each includes a distal end inner hole 21, a middle section inner hole 22 and a proximal end inner hole 23. Medical guide wires can extend through the distal end inner holes 21 from the proximal end to the distal end, and are used for guiding the medical device implantation apparatus to reach the desired position. The inner sheath 2 can be fixed in the middle section inner holes 22. The distal end inner hole 21 and the middle section inner hole 22 can be designed as two parts separately or as an integral part. Compression stent branches 31 and 32 are fixed in the proximal end inner holes 23.

The inner sheath 2 includes a first inner sheath 15 and a second inner sheath 16. The first outer casing 11 and the second outer casing 12 respectively wrap and fix the distal end of an inner sheath 2. The first outer casing 11 and the second outer casing 12 are located on the outer side of the distal end of the inner sheath 2. A curved angle structure with a certain arc is formed at the connection between the end surface of the distal end of the outer casing 1 and the side wall of the outer casing 1 to avoid damage to a human body lumen during use. The first inner sheath 15 and the second inner sheath 16 are arranged side by side, and the medical guide wires can respectively pass through the interiors of the first inner sheath 15 and the second inner sheath 16. The distal ends of the first inner sheath 15 and the second inner sheath 16 are respectively wrapped by the first outer casing 11 and the second outer casing 12. The proximal ends of the first inner sheath 15 and the second inner sheath 16 are connected to the adjusting handle 9 through the rear handle part 8. The first inner sheath 15 and the second inner sheath 16 are of hollow structures, and the guide wires can pass through the interiors of the inner sheath 15 and the second inner sheath 16. In addition, the inner sheath 2 can also be designed as a distal end bifurcation structure, and portions of the distal end bifurcation structure are connected to the first outer casing 11 and the second outer casing 12 respectively.

The middle sheath 3 covers at least part of the inner sheath 2. The distal end of the middle sheath 3 is abutted against the proximal end of a stent main branch 30 to limit the position of the stent. The proximal end of the middle sheath 3 can be designed to be connected to the rear handle part 8, or the proximal end of the middle sheath 3 is connected to the booster sheath 5. The booster sheath 5 is of a hollow structure, and the distal end of the booster sheath 5 is fixedly connected to the proximal end of the middle sheath 3. The booster sheath 5 is made of metal, which helps to transmit force when the medical device is released. The proximal end of the booster sheath 5 is connected to the rear handle part 8. As the middle sheath 3 is made of polymer plastic, the middle sheath 3 is relatively soft; and the booster sheath 5 is made of metal, such as medical stainless steel. Therefore, the middle sheath 3 has good flexibility and bendability when entering the human body lumen, and the booster sheath 5 is helpful for the transmission of force during the implantation and release of the medical device. A developing part 13 is arranged on the outer wall of the distal end of the middle sheath 3. The developing part 13 can be embedded on the outer wall of the middle sheath 3 or placed on the outer surface of the middle sheath 3 in other ways, which facilitates the positioning and release of the medical device during the operation.

The outer sheath 4 is located on the outer side of the middle sheath 3, covers at least part of the middle sheath 3, and is movable relative to the inner sheath 2. The proximal end of the outer sheath 4 is connected to a front handle part 7. The outer side of the outer sheath 4 can be surrounded by soft materials, so that during surgery, especially when the outer sheath turns a corner, the irritation to the human body lumen can be reduced.

The handle 6 is located at the proximal end of the medical device implantation apparatus and comprises the front handle part 7, the rear handle part 8 and the adjusting handle 9. The front handle part 7 is located at the distal end of the handle 6 and is connected to the proximal end of the outer sheath 4. The proximal end of the front handle 7 is provided with a safety lock 10 composed of a locking screw and a locking nut. The front handle part 7 can be fixed on the booster sheath 5 by screwing, and plays a role in positioning. The rear handle part 8 is located between the front handle part 7 and the adjusting handle 9 and is connected to the proximal end of the booster sheath 5. The adjusting handle 9 is located at the proximal end of the medical device implantation apparatus, and is connected to the tail end of the proximal end of the inner sheath 2. A positioning lock 14 is arranged between the front handle part 7 and the rear handle part 8 and covers the boost sheath 5.

Figure 4:
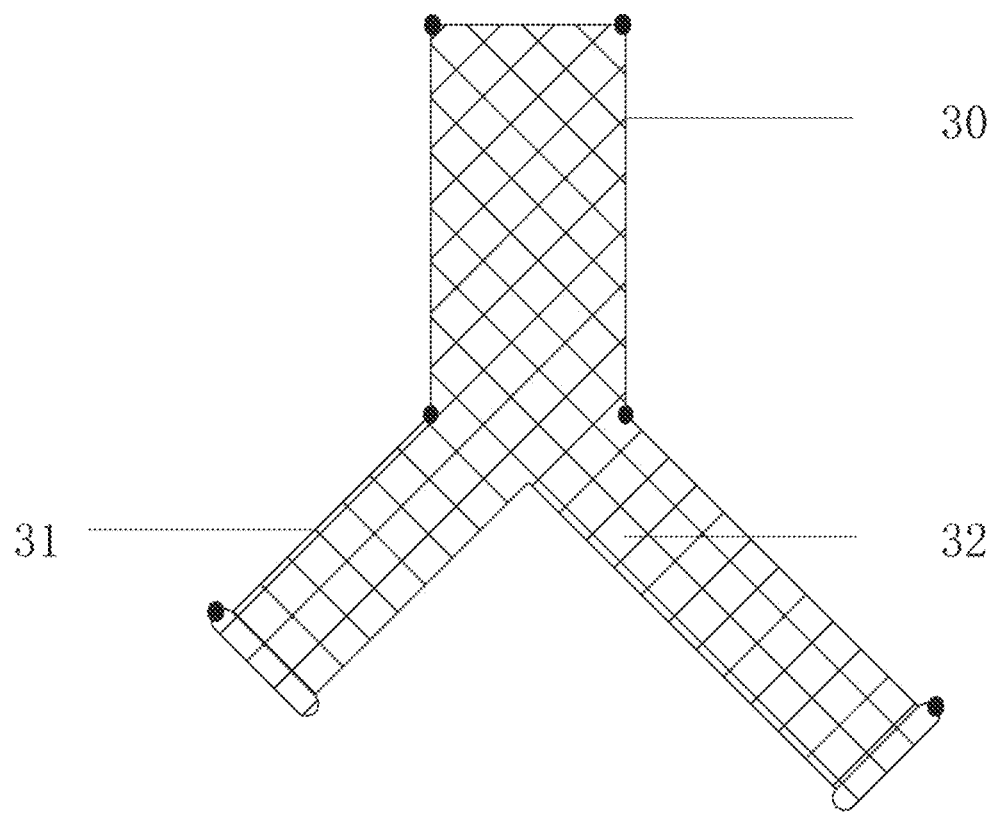
FIG. 4 is a schematic diagram of a Y-shaped stent used in cooperation with the medical device implantation apparatus.

The outer casing 1 can be used for compressing the stent. The stent can include the stent main branch 30 and the stent branches 31 and 32. The two stent branches 31 and 32 can be the same in length or different in length. As shown in FIG. 4, the two stent branches 31 and 32 of the stent are different in length. As the first inner sheath 15 and the second inner sheath 16 are different in length, the two branches 31 and 32 of the stent are respectively sleeved on the first inner sheath 15 and the second inner sheath 16, thereby being compressed into the first outer casing 11 and the second outer casing 12 respectively. The stent branches 31 and 32 are confined in the proximal end inner holes 23 of the outer casing 1.

The medical device implantation apparatus of the present invention can convey including but not limited to the self-expandable stent, and can also convey other medical devices that can be released from the implantation apparatus by withdrawing the outer sheath 4 relative to the inner sheath 2.

Figure 5:
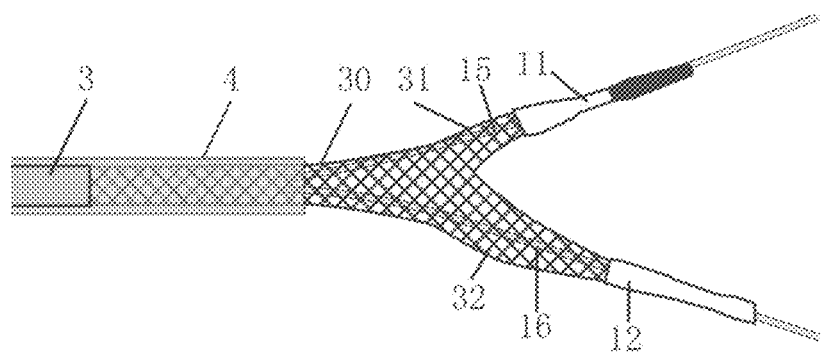
FIG. 5 to FIG. 7 are schematic diagrams showing the process of implanting a medical device by the medical device implantation apparatus.
Figure 6:
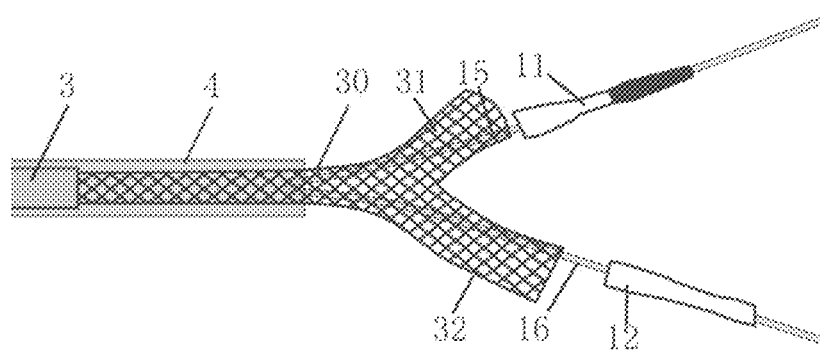
Figure 7:
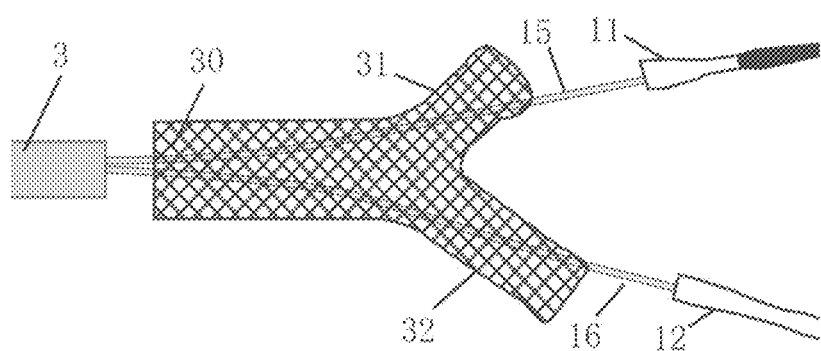

As shown in FIG. 5 to FIG. 7, the implantation process of the medical device implantation apparatus is as follows: firstly, the distal ends of the two stent branches 31 and 32 of the stent are respectively compressed and placed into the outer casing 1; then the main stent 30 covers the inner sheath 2, and the positioning lock 14 is locked, so that the main stent 30 is fixed on the booster sheath 5; after the outer sheath 4 covers the stent main branch 30 and the stent branches 31 and 32, the safety lock 10 is screwed, and the stent assembly is completed. When the positioning lock 14 is fixed, the position of the positioning lock is close to the safety lock 10, and can prompt the doctor that when the front handle part 7 is withdrawn to the positioning lock 14, the stent branches 31 and 32 are released from the outer sheath 4.

When the medical device implantation apparatus is in use, firstly, the two medical guide wires pass through the inner sheath 2 respectively, and under the guidance of the medical guide wires, the medical device implantation apparatus reaches the position of the lesion, and at the moment, the safety lock 10 and the positioning lock 14 are both locked. The safety lock 10 of the medical device implantation apparatus is unscrewed, the rear handle part 8 and the adjusting handle 9 are fixed, the front handle part 7 is withdrawn, and thus, the outer sheath 4 is driven to withdraw, so that the stent branches 31 and 32 assembled in the outer sheath 4 are output from the outer sheath 4. When the included angle between the two branches 31 and 32 of the stent is against a bulge, the safety lock 10 is screwed. Then the front handle part 7 and the rear handle part 8 are fixed, the adjusting handle 9 is pushed forward, and the adjusting handle 9 drives the inner sheath 2 to move to the distal end, thereby driving the outer casing 1 to move towards the distal end to separate the distal ends of the stent branches 31 and 32 from the outer casing 1. At the moment, the bifurcation of the branch abuts against the human body lumen, the safety lock 10 and the positioning lock 14 are unscrewed, the rear handle part 8 is fixed, and the front handle part 7 is withdrawn, so that the stent main branch 30 is partially pushed out of the outer sheath 4, and the medical device release process is completed.

The above are only the preferred embodiments of the present invention, and do not limit the present invention in any form. Although the present invention has been disclosed in the preferred embodiments as above, the preferred embodiments are not intended to limit the present invention. Anyone skilled in the art can use the technical content disclosed above to make slight changes or decoration into equivalent embodiments with equivalent changes without departing from the scope of the technical solution of the present invention, but any content that does not depart from the technical solution of the present invention, and any simple modifications, equivalent changes and decoration made to the above embodiments according to the technology essence of the present invention still fall within the scope of the technical solution of the present invention.

What is claimed is:

1. A medical device implantation apparatus, comprising:
   an outer sheath, extending from a proximal end to a distal end, the proximal end of the outer sheath being connected to a front handle part of a handle;
   a middle sheath, the middle sheath being arranged in the outer sheath, and a proximal end of the middle sheath being connected to a rear handle part of the handle;
   an inner sheath, the inner sheath being allowed to pass through the middle sheath, a proximal end of the inner sheath being connected to an adjusting handle third portion of the handle, and the inner sheath being movable relative to the outer sheath; and
   outer casings, with at least two outer casings being provided, and a distal end of the inner sheath being respectively fixedly connected to the outer casings;
   wherein the rear handle part is located between the front handle part and the adjusting handle of the handle, and a positioning lock is arranged between the front handle part of the handle and the rear handle part of the handle, the positioning lock being arranged to prompt a user that when the front handle part is withdrawn to the positioning lock, a distal end of a medical device to be implanted is released from the outer sheath; and
   the medical device to be implanted is arranged around the inner sheath, with the distal end of the medical device being accommodated in the outer casings, and a proximal end of the medical device being accommodated in the outer sheath and abutting against a distal end of the middle sheath, wherein the inner sheath moves relative to the outer sheath by manipulating the adjusting handle of the handle to release the medical device.

2. The medical device implantation apparatus according to claim 1, wherein each outer casing comprises a part for fixing the inner sheath and a part for fixing the medical device.

3. The medical device implantation apparatus according to claim 1, wherein the inner sheath has a distal end bifurcation structure that is respectively connected to the outer casings.

4. The medical device implantation apparatus according to claim 1, wherein the inner sheath comprises a first inner sheath and a second inner sheath which are distributed side by side, and tail ends of the distal end of the inner sheath are respectively connected to the outer casings.

5. The medical device implantation apparatus according to claim 4, wherein the first inner sheath and the second inner sheath are the same in length or different in length.

6. The medical device implantation apparatus according to claim 1, wherein the medical device is a stent.

7. The medical device implantation apparatus according to claim 1, wherein the middle sheath is connected to the rear handle part of the handle through a booster sheath, and the positioning lock covers the booster sheath.

8. The medical device implantation apparatus according to claim 7, wherein the booster sheath is made of metal.

9. A method of using the medical device implantation apparatus according to claim 1, comprising:
   withdrawing the front handle part of the handle towards a proximal end, and part of the medical device is released from the outer sheath;
   pushing the adjusting handle of the handle towards a distal end, and the medical device is separated from the outer casings; and
   withdrawing the front handle part of the handle finally, and the medical device is released and implanted.

* * * * *